US00PP33622P2

(12) United States Plant Patent
Zaiger et al.

(10) Patent No.: US PP33,622 P2
(45) Date of Patent: Nov. 9, 2021

(54) INTERSPECFIC ALMOND TREE NAMED 'ALM-754'

(50) Latin Name: ***Prunus* species**
Varietal Denomination: ALM-754

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 17/300,364

(22) Filed: Jun. 1, 2021

(51) Int. Cl.
*A01H 5/08* (2018.01)
*A01H 6/74* (2018.01)

(52) U.S. Cl.
USPC ..... Plt./155

(58) Field of Classification Search
USPC ..... Plt./155
See application file for complete search history.

*Primary Examiner* — Susan McCormick Ewoldt

(57) ABSTRACT

A new and distinct variety of interspecific almond tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. The tree being self-fertile with the ability to produce almonds without the use of pollinators.
2. Vigorous, upright growth of tree.
3. Producing nuts that are well sealed and soft shelled.
4. Nuts having very good eating quality.
5. Nuts harvesting approximately 5 to 10 days after 'Nonpareil' Almond (non-patented).

1 Drawing Sheet

Botanical designation: *Prunus* species.
Variety denomination: 'ALM-754'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

Prior Varieties

Among the existing varieties of almond trees, which are known to us, and mentioned herein, 'Nonpareil' Almond (non-patented), 'Alm-21' Almond (U.S. Plant Pat. No. 20,295), 'Jordanola' Almond (non-patented) and the proprietary almond seedlings '33HD174', '301LU163', 'Dwf#14', '13Z64' and our proprietary interspecific seedling '81GE109'.

STATEMENT REGARDING FEDERALLY SPONSORED RESEARCH AND DEVELOPMENT

Not applicable.

ORIGIN OF THE VARIETY

The new and distinct variety of interspecific almond tree was originated by us in our experimental orchard located near Modesto, Calif. as a first-generation cross between our proprietary non-patented interspecific almond variety '33HD174' and our proprietary almond variety '301LU163'. The seed parent '33HD174' originated as a first-generation cross between our proprietary non-patented almond selection 'Dwf#14' and our proprietary non-patented interspecific seedling selection '81GE109'. The pollen parent '301LU163' originated as a first-generation cross between 'Jordanola' Almond (non-patented) and the proprietary almond seedling '13Z64'. A large group of these first-generation seedlings were grown and budded onto older trees of 'Nemaguard' Rootstock (non-patented) to accelerate rapid nut production for evaluation. Under close and careful observation, one such seedling, which is the present variety, exhibited desirable nut and tree characteristics and was selected in 2012 for additional asexual propagation and commercialization.

ASEXUAL REPRODUCTION OF THE VARIETY

In 2012 asexual reproduction of the new and distinct variety of interspecific almond tree was by budding to 'Nemaguard' Rootstock (non-patented), as performed by us in our experimental orchard located near Modesto, Calif., and shows that reproductions run true to the original tree and all characteristics of the tree and its nuts are established and transmitted through succeeding asexual propagations.

SUMMARY OF THE NEW VARIETY

The present new and distinct variety of interspecific almond tree is of large size, vigorous, upright growth and a productive and regular bearer of soft shell nuts with kernels having a very good flavor. The harvest maturity for knocking, (shaking the nuts from the tree), is approximately 5-10 days after the leading almond variety 'Nonpareil' Almond (non-patented) and the nuts release from the tree readily. The soft shell of the nut is well sealed, readily hulled and shelled, similar to 'Nonpareil' Almond (non-patented). The low percentage of doubles, usually less than 5%, under growing conditions prevailing in our area, Stanislaus County, Calif. The primary difference between the new variety and 'Nonpareil' Almond (non-patented) is the new variety is self-fertile and 'Nonpareil' Almond (non-patented) is self-sterile and needs a pollinator tree planted near to fertilize the flowers to produce almonds. In comparison to its proprietary non-patented interspecific seed parent '33HD174' the kernel of the new variety is larger in size and its harvest maturity is approximately 15 days later. In comparison to its proprietary non-patented pollen parent '301LU163' the harvest maturity of the new variety is approximately 5 days later. In comparison to the commercial variety 'Alm-21' Almond (U.S. Plant Pat. No. 20,295) the new variety harvest starts approximately 10-15 days later.

DESCRIPTION OF THE PHOTOGRAPH

The accompanying color photographic illustration shows typical specimens of the flowers, foliage and nuts of the present new interspecific almond variety at 8 years of age. The illustration shows a typical flower inset, the upper and lower surface of the leaves, a spur with a cluster of nuts, 2 nuts with mature hulls showing the splitting, dried, light brown condition at harvest time, two individual nuts are shown without hulls and kernels are shown without shells. The photographic illustration was taken shortly after being harvested and the colors are as nearly true as is reasonably possible in a color representation of this type.

DESCRIPTION OF THE VARIETY

The following is a detailed botanical description of the new variety of interspecific almond tree, its flowers, foliage and nuts, as based on observations of 8 year old specimens grown near Modesto, Calif., with color in accordance with Munsell Book of Color published in 1958.

Tree:

- *Size*.—Large, normal for commercial almond trees. Height approximately 4 meters, width 3 meters. Varies slightly with type and fertility of soil.
- *Vigor*.—Vigorous, tree growth of 1.5 to 2 meters the first growing season. Varies with cultural practices, soil type, fertility and climatic conditions.
- *Form*.—Upright growth, similar to the 'Nonpareil' Almond (non-patented).
- *Branching habit*.—Upright, crotch angle approximately 35°, increases with heavy crop load.
- *Productivity*.—Productive, comparable to 'Nonpareil' Almond (non-patented). Varies with type and fertility of soil.
- *Bearer*.—Regular, heavy crop load 6 consecutive years, no alternate bearing observed.
- *Fertility*.—Self-fertile.
- *Density*.—Medium dense, usually pruned to open center of tree allowing more sunlight to enhance health of nut bearing spurs.
- *Hardiness*.—Hardy in all almond growing areas of California. Tree grown in USDA Hardiness Zone 9. Winter chilling requirement approximately 450 hours at or below 45° F. Blooming approximately 5 days after 'Nonpareil' Almond (non-patented) in our experimental orchard.

Trunk:

- *Size*.—Medium, average circumference 63.5 cm at 25.4 cm above ground on an 8 year old tree.
- *Stocky*.—Medium stocky.
- *Texture*.—Medium shaggy, roughness increases with age of tree.
- *Color*.—Varies from 5Y 4/2 to 5Y 2/2.

Branches:

- *Size*.—Medium, normal for almond trees. Average circumference 18.8 cm at 1 meter above ground.
- *Surface texture*.—New growth smooth, varies to medium rough with age.
- *Lenticels*.—Average number 123 in a 25.8 square cm area. Average length 1.9 mm. Average width 1.1 mm. Color varies from 5YR 5/6 to 5YR 4/6.
- *Color*.—New growth varies from 2.5GY 6/8 to 2.5GY 5/8. Old growth varies from 7.5YR 4/12 to 7.5YR 2/4, becomes darker with age.

Leaves:

- *Size*.—Medium. Average length 89.6 mm. Average width 26.9 mm.
- *Form*.—Elliptical.
- *Apex*.—Acuminate.
- *Base*.—Cuneate.
- *Margin*.—Crenate.
- *Thickness*.—Medium, normal for almonds.
- *Surface texture*.—Upper surface relatively smooth, very slight indentations over midrib and leaf veins. Lower surface relatively smooth, with small ridges created by midrib and pinnate venation. Both upper and lower surfaces glabrous.
- *Petiole*.—Average length 24.5 mm. Average width 1.3 mm. Longitudinally grooved. Surface — glabrous. Color varies from 5GY 7/6 to 5GY 6/6.
- *Glands*.—Type — globose. Size — small. Average length 0.5 mm. Average diameter 0.3 mm. Average number 2, varies from 1 to 3. Located primarily on the base of the leaf blade and upper portion of the petiole. Color varies from 5GY 6/4 to 5GY 4/4.
- *Stipules*.—None present at time of measurement.
- *Venation*.—Pinnately veined.
- *Color*.—Upper surface varies from 5GY 4/4 to 5GY 3/4. Lower surface varies from 5GY 4/4 to 5GY 4/6. Midvein color varies from 5GY 7/6 to 5GY 8/6.

Flower buds:

- *Size*.—Medium to large. Average length 16.2 mm. Average diameter 8.1 mm.
- *Hardiness*.—Hardy in all almond growing areas of California.
- *Density*.—Dense.
- *Form*.—Elongated
- *Pedicel*.—Average length 3.3 mm. Average width 2.0 mm. Color varies from 2.5GY 6/6 to 5GY 7/6.
- *Color*.—Varies from 7.5RP 9/2 to 10RP 9/2.
- *Number of buds per spur*.—Average number 12, varies from 7 to 14.

Flowers:

- *Blooming period*.—Date of First Bloom Feb. 20, 2020. Date of Petal Fall Mar. 3, 2020, varies slightly with climatic conditions.

*Size*.—Large. Average height 17.1 mm. Average diameter 45.4 mm.

*Petals*.—Normally five, alternately arranged to sepals. Shape — obovate, apex undulated, base narrows at point of attachment. Average length 21.3 mm. Average width 16.0 mm. Margin — sinuate. Both upper and lower surfaces glabrous. Color varies from N 9.5/(white) to 5RP 9/2.

*Sepals*.—Normally five, alternately arranged to petals. Shape — triangular, apex rounded. Average length 7.2 mm. Average width 5.5 mm. Margin — entire. Upper surface glabrous, lower surface pubescent. Color — upper surface varies from 5GY 5/6 to 5R 3/8. Lower surface varies from 5GY 5/6 to 7.5R 2/2.

*Stamens*.—Average number per flower 37. Average filament length 12.2 mm. Filament color N 9.5/(white) to 5RP 5/8 as flower ages. Anther color varies from 5Y 8/6 to 5Y 8/8. On average, the stamens are below the height of the petals.

*Pollen*.—Self-fertile. Color varies from 5Y 7/10 to 5Y 7/12.

*Pistil*.—Normally one. Surface — pubescent. Average length 13.0 mm. Position of stigma an average of 1.7 mm below anthers. Color varies from 10Y 7/6 to 2.5GY 7/6.

*Fragrance*.—Heavy aroma.

*Number flowers per flower bud*.—One.

*Pedicel*.—Average length 4.2 mm. Average width 2.0 mm. Color varies from 2.5GY 7/8 to 5GY 6/6.

*Color*.—Varies from 10RP 9/2 to N 9.5/(white), fades with age of flower.

Nut crop:

*Productivity*.—Very heavy, beginning in 3rd leaf.

*Maturity when described*.—Hull split, when abscission layer formed between spur and nuts.

*Date of harvest period*.—September 1 through September 10, varies slightly with climatic conditions. Approximately 5 to 10 days after 'Nonpareil' Almond (non-patented) harvest.

*Distribution*.—Well distributed throughout the tree.

*Tenacity*.—Hangs well until harvest time.

Hull:

*Surface*.—Relatively smooth, short pubescence.

*Form*.—Elliptical.

*Thickness*.—Average 1.6 mm when dry.

*Flesh*.—Leathery, becomes brittle when dry.

*Suture*.—Minimal, relatively smooth.

*Color*.—Varies from 2.5GY 7/8 to 7.5Y 6/2 during growing season. Varies from 7.5RP 4/2 to 10RP 5/2 when dry.

*Dehiscence*.—Good, opens freely, splitting along suture.

*Nut cavity*.—Oval.

*Adherence*.—Hulls easily removed from nuts by mechanical huller.

Shell:

*Size*.—Large. Average length 34.1 mm. Average width 19.6 mm. Average thickness 13.7 mm.

*Shape*.—Elongated, ovate.

*Thickness*.—Classified as paper shell, (i.e. easy to crack).

*Color*.—Outer color varies from 10YR 7/6 to 10YR 5/6. Inner color varies from 10YR 7/4 to 10YR 6/6.

*Surface*.—Outer surface covered with randomly spaced, small, shallow, round pits. One very small, shallow, long groove on each side of the well sealed suture, extending from base to apex. Inner surface covering the kernel is smooth. Shell easily removed from kernel by mechanical sheller.

*Apex*.—Pointed, acuminate. Average length 1.7 mm.

*Base*.—Flat.

*Stem scar*.—Large in size. Wing- thin, extends from base to apex. Percent of kernel to nut, approximately 80%.

Kernel:

*Size*.—Large. Average length 24.9 mm. Average width 12.0 mm. Average thickness 7.5 mm. Average weight 1.3 grams, varies slightly with fertility of the soil and climatic conditions.

*Form*.—Ovate.

*Shape*.—Slightly thick to flat, elongated. Base rounded. Apex acuminate, slight point, average 1.1 mm.

*Surface texture*.—Slightly wrinkled on some kernels, otherwise smooth, similar to 'Nonpareil' Almond (non-patented).

*Pellicle*.—Medium size.

*Color*.—Varies from 10YR 5/8 to 10YR 5/10.

*Number of doubles*.—Very low, usually less than 5%. Varies slightly with fertility, climatic conditions and cultural practices.

*Flavor*.—Very good, sweet.

*Quality*.—Very good.

Use:

*Market*.—Local and long distance.

Keeping quality: Good, will store for 1 year with no breakdown of kernel in appearance or flavor.

Shipping quality: Good, comparable to 'Nonpareil' Almond (non-patented).

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices.

The present new variety of interspecific almond tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific almond tree, substantially as illustrated and described.

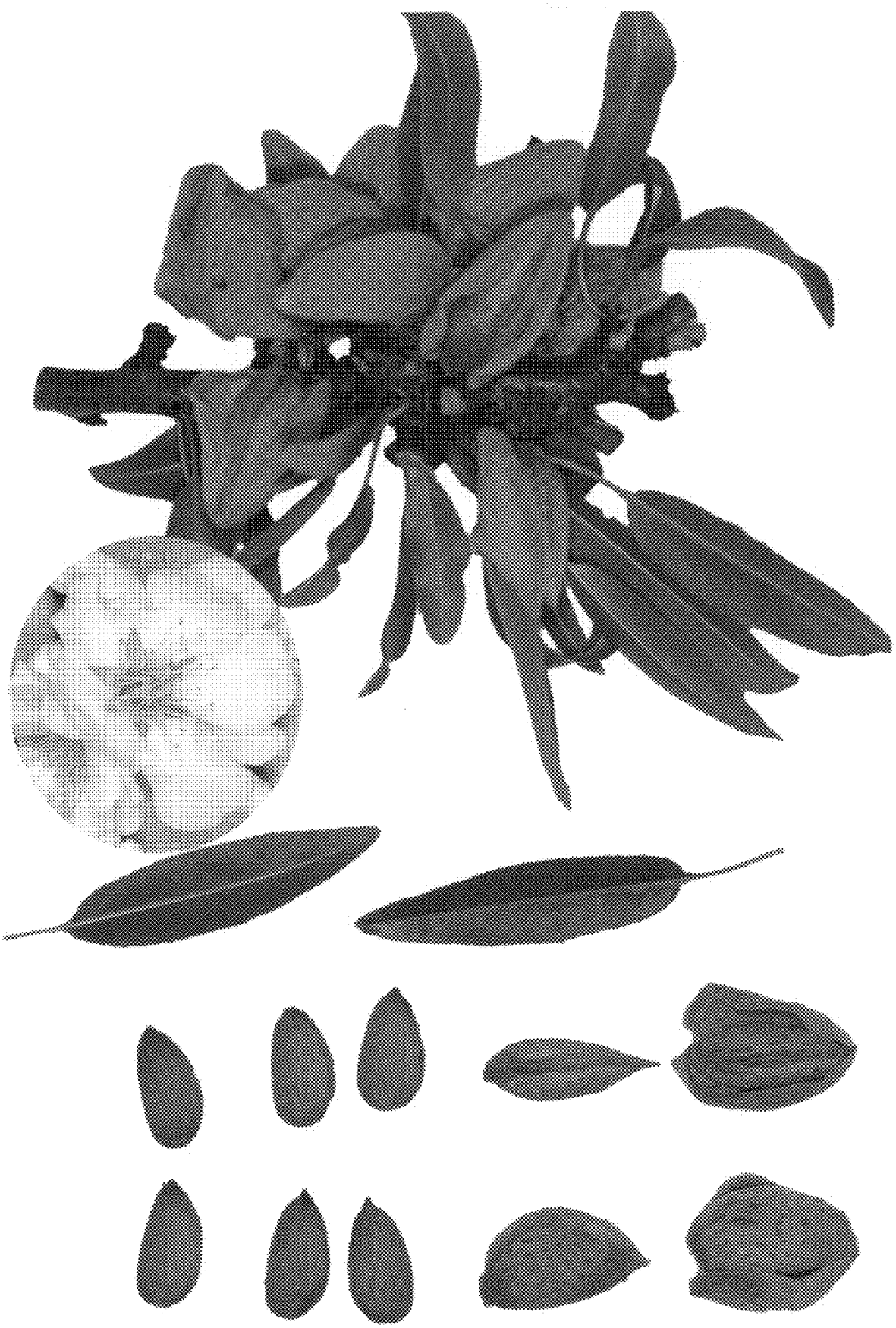

* * * * *